United States Patent [19]

Single et al.

[11] Patent Number: 5,584,870
[45] Date of Patent: Dec. 17, 1996

[54] IMPLANT ESD PROTECTION NETWORK

[75] Inventors: Peter Single, Lane Love; Kenneth R. Dickson, Mt. Colau; David Money, Pennant Hills, all of Australia

[73] Assignee: Cochlear Ltd., Lane Cove, Australia

[21] Appl. No.: 401,468

[22] Filed: Mar. 9, 1995

[51] Int. Cl.⁶ .............................. H04B 15/00; A61N 1/08
[52] U.S. Cl. .................................. 607/63; 607/57; 607/60; 607/2
[58] Field of Search .................................. 607/55–57, 60, 607/2, 30–32; 128/901, 746, 903, 908

[56] References Cited

U.S. PATENT DOCUMENTS

| | | | |
|---|---|---|---|
| 3,920,025 | 11/1975 | Stasz et al. | 607/63 |
| 4,515,158 | 5/1985 | Patrick et al. | 607/60 |
| 4,592,359 | 6/1986 | Galbraith | 607/63 |
| 5,070,535 | 12/1991 | Hochmair et al. | 607/57 |
| 5,095,904 | 3/1992 | Seligman et al. | 607/57 |
| 5,197,468 | 3/1993 | Proctor et al. | 607/9 |

*Primary Examiner*—William E. Kamm
*Assistant Examiner*—Kennedy J. Schaetzle
*Attorney, Agent, or Firm*—Gottlieb, Rackman & Reisman

[57] ABSTRACT

A protective component is provided for protecting a cochlear implant from external electrostatic discharges. The implant receives signals through a receiver coil inductively coupled to a transmitter coil. The protective component is disposed across the coil of the transmitter.

11 Claims, 1 Drawing Sheet

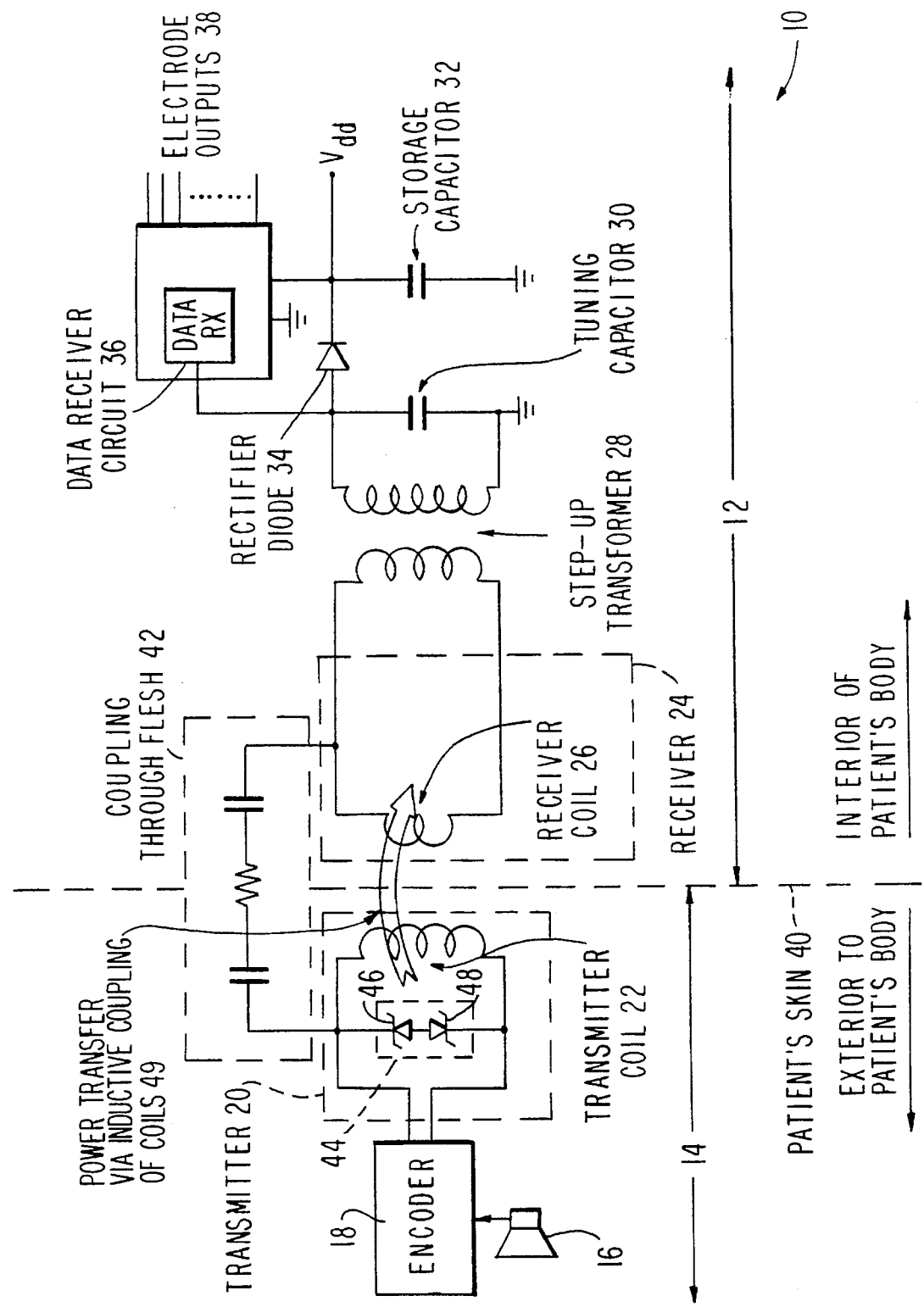

IMPLANT ESD PROTECTION NETWORK

BACKGROUND OF INVENTION

A. Field of Invention

This invention pertains to implantable devices used to provide various types of therapy, and more particularly, to such devices having protection means from high energy ambient electrical interference such as electrostatic discharge (ESD).

B. Description of the Prior Art

Implantable electronic devices are used to provide therapy to patients suffering from a wide range of health problems. For example, cochlear devices are used to aid people suffering acute loss of hearing. Pacemakers and cardioversion/defibrillation devices are used to aid patients with cardiac arrhythmias.

Since these devices, when implanted, are immersed in fluids which are highly electrolytic and, since they are provided in an electrically conductive casing, one would expect that they would be well shielded from ambient electrical interference. In fact, a very large number of such devices have been implanted and in use for the last twenty years and the number of failures attributed to any ambient electrical interference has been minimal. However, there has been a small number of instances known to the inventors where cochlear implants have failed, apparently due to high energy level ambient electromagnetic fields.

Thus, it appears that there is a need for improving the protection of implantable devices from ambient electromagnetic interference. Moreover, since a large number of such devices have already been implanted, it would be beneficial to have a means of increasing the protection of the implanted devices in a manner which does not require explantation.

OBJECTIVES AND SUMMARY OF THE INVENTION

In view of the above, it is an objective of the present invention to provide an implant system with protection means against ambient electromagnetic interference, said protection means being disposed outside the implanted device.

A further objective is to provide a system in which the protection means is completely passive so that it does not interfere with the normal operation of the device.

Yet another objective is to provide a protective means which is relatively inexpensive and easy to implement to reduce the costs of a new design and/or retrofit.

Other objectives and advantages of the invention shall become apparent from the following description.

Implantable devices can be grouped into three categories. The first category consists of devices which require substantially continuous communication between the implant and an external component. Cochlear devices fall into this category since they require continuous signal transmission from a speech processor so that the patient can sense external sounds.

The second category consists of devices which normally operate independently, however, at regular or preset intervals they do exchange information with an external component to receive new or updated programming or to download information. Pacemakers and cardioversion/defibrillator devices fall into this second category.

The third category consists of devices which, after implantation, operate without any communication with the outside world. As shall be seen from the discussion below, the present invention is applicable primarily to devices of the first and second categories.

The term "cochlear device" as used in this application refers to a device consisting of an external speech processor and an implant. The external speech processor receives ambient sounds, converts the sounds into electrical signals and transmits these signals via a transmitter coil by electromagnetic induction to the implant. The implant applies these signals to the auditory nerve of the patient.

As previously mentioned, the problem addressed by this invention arose with cochlear devices. More particularly, a small number of cochlear devices failed and, on explantation, it was found that several of the elements associated with the data receiving function were damaged by a high level electrical shock. A number of experiments were performed in a laboratory to try to induce similar failures in other cochlear devices. More particularly, implants were submersed in a saline solution simulating body fluids and tissues, and subjected to high level electromagnetic fields so as to produce electrostatic discharge (ESD) into the implant.

ESD was the primary suspect for causing the failures because one failure was reported after the patient (a child) used a slide in a playground and the inventors noted that on very dry days children using slides became electrostatically charged to about 15 KVDC.

In one experiment, electrical shocks were applied to the surface of the saline solution. As expected, the saline solution attenuated the shocks and protected the implant from damage.

In another experiment, electrical conductors were connected to the metal casing of the implant and electrical shocks were applied to the conductors. These shocks did damage some of the elements of the implant, but not in a manner that matched the damage found in the failed devices.

Surprisingly, it was discovered, however, that the mode of failure was replicated exactly when the transmitter coil of a speech processor was placed adjacent to the implant and ESD pulses were applied to the conductors connected to the transmitter coil. Thus, the present inventors have discovered that electrostatic discharge to the transmitter coil of the external speech processor was transmitted by electromagnetic coupling to the implant where its high intensity and energy contents damaged the implant's receiver elements. Importantly, ESD protection, according to this invention, can be provided to the external speech processor to protect the internal implant.

A device constructed in accordance with this invention includes an internal portion for providing therapy, such as a cochlear implant, and an external portion, such as a speech processor. The external portion is provided with a transmitter coil and the internal portion has a receiver coil arranged so that when the two coils are in close proximity, electrical signals are sent from the transmitter to the receiver coil. Importantly, the external device is provided with an ESD suppressing means for suppressing ESD pulses thereby insuring that they are not transmitted to the receiver coil.

BRIEF DESCRIPTION OF THE DRAWING

The single FIGURE is a schematic diagram of a cochlear implant system incorporating the present invention.

DETAILED DESCRIPTION OF THE INVENTION

Referring now to the single figure, a cochlear device 10 constructed in accordance with this invention includes an implantable or internal portion 12, which in this case is a cochlear implant, and an external portion, which in this case is a speech processor 14. The speech processor includes a microphone 16, an encoder 18 and a transmitter 20. It should be understood that the transmitter 20 has a number of elements of which only transmitter coil 22 is shown for the sake of clarity.

The cochlear implant 12 includes a receiver 24. Again, this receiver includes various elements, of which only the receiver coil 26 is shown. Device 14 further includes a step-up transformer 28, a tuning capacitor 30, a power storage capacitor 32, and a diode 34. The device 12 further includes a data receiver circuit 36, with a plurality of electrode output lines 38.

The system 10 described so far is fairly conventional and operates as follows.

The cochlear implant 12 is implanted into a patient with the receiver coil 26 disposed subcutaneously near skin 40.

The external device 14 is disposed outside the body with the transmitter coil 22 positioned adjacent to the receiver coil 26 so that the skin 40 extends therebetween.

With the exception of receiver 26, Device 12 is disposed in an insulated metal casing, which has been omitted in the figure.

Ambient sounds are picked up and converted into corresponding electrical signals by microphone 16. These signals are encoded by encoder 18. The transmitter 20 receives the encoded signals and transmits them through the coils 22, 26 to receiver 24. The received signals are received by data receiver circuit 36 and translated into impulses for the electrode outputs 38. The wearer is trained so that he can recognize the sounds picked up by microphone 16 through the corresponding signals appearing on electrodes 38.

Diode 34 is used to charge capacitor 32 which acts as a temporary power supply to provide power to the data receiver circuit 36 and other components of the implant (not shown).

When the coils 22, 26 are disposed in the opposing relation shown in the figure, they are coupled electromagnetically by the mutual inductance 49 between the coils. In addition, a leakage path exists across the skin 40 between the coils 22, 26, represented symbolically in the figure by a series capacitor-resistor combination 42. However, this path does not play a part in the normal operation of the system.

As previously described, the present inventors have discovered that ESD pulses can be picked up by portion 14 and transmitted from coil 22 to coil 26. Since the energy content of these extremely short duration pulses is very high, they could damage various elements of the implant 12.

In order to prevent this damage, a protective device 44 is provided in the transmitter 20. This device 44 is used to suppress the ESD pulses so that they do not propagate to the implant portion 12. For example, as shown in the figure, the protective device could consist of a pair of Zener diodes 46, 48 connected back-to-back, as shown. Other ESD suppressing components are known which could be provided in the device 12 such as, for example, diodes connected from various internal inputs and outputs of device 12 to ground and/or the power supply (i.e., storage capacitor 32). However, such an implementation would take up precious space within the implant, increase the component count and consequently decrease the reliability of the device (a concern which is critical in an implanted device). Moreover, devices already implanted could not be protected by the addition of these diodes, without being explanted and replaced.

The present invention in the external portion provides a much more effective solution. This arrangement is much easier to implement. Moreover, existing implanted devices could be easily retrofitted, since only the external portion need be modified. The actual protection device 44 is standard in the art, and other transient suppressing mechanisms could be employed. What is unusual about the overall arrangement is that applying the mechanism to the transmitter protects the receiver.

Although the invention has been described with reference to a preferred embodiment, it is to be understood that this embodiment is merely illustrative of the application of the principles of the invention. Accordingly, the embodiment described in particular should be considered exemplary, not limiting, with respect to the following claims.

We claim:

1. A device for providing therapy to a patient comprising:
   an implantable portion for implantation in the patient, said implantable portion including a receiver for receiving signals;
   an external portion for generating signals, said external portion including a transmitter for transmitting signals to said receiver when said external portion is positioned to provide inductive coupling between said transmitter and said receiver; and
   a protective device disposed in said transmitter provided to suppress the effect of electrostatic discharge to prevent propagation of said discharge energy to said implantable portion.

2. The device of claim 1 wherein said implantable portion is a cochlear implant.

3. The device of claim 2 wherein said external device is a speech encoder.

4. The device of claim 1 wherein said receiver and transmitter include respective coils.

5. The device of claim 1 wherein said protective device is electrically connected across said transmitter coil.

6. A device for providing therapy to a patient, comprising:
   an implantable portion for implantation in a patient, said implantable portion including a receiver for receiving electrical signals; and
   an external portion for generating said electrical signals, said external portion including a transmitter having a transmitter coil adapted to transmit said signals to said receiver by magnetic induction when said transmitter is positioned adjacent to said receiver;
   said external portion further including a protective device electrically coupled across said transmitter coil and arranged to suppress undesirable transient signals from propagating from said transmitter to said receiver.

7. The system of claim 6 wherein said said receiver includes a receiver coil, said coils being inductively coupled when said transmitter is positioned adjacent to said receiver.

8. The system of claim 7 wherein said protective device includes means for suppressing the damaging effects of electrostatic discharges.

9. The system of claim 8 wherein said implantable portion is a cochlear implant and said external portion is a speech processor.

10. A method of protecting a therapeutic device from electrostatic discharges, said device including an implantable portion having a receiver for receiving signals related to therapy, and an external portion generating said signals and including a transmitter for inductive transmission of said signals to said receiver when said transmitter and receiver are adjacent, said transmitter including a protective device disposed therein, said method comprising
    suppressing undesirable electromagnetic interference in said transmitter with said protective device to prevent said interference from damaging said implantable portion.

11. The method of claim 10 wherein said suppressing is performed by said protective device by suppressing electrostatic discharges.

* * * * *